(12) United States Patent
Utley et al.

(10) Patent No.: US 7,458,378 B2
(45) Date of Patent: *Dec. 2, 2008

(54) SYSTEMS METHODS FOR APPLYING A SELECTED TREATMENT AGENT INTO CONTACT WITH TISSUE TO TREAT SPHINCTER DYSFUNCTION

(75) Inventors: David S Utley, San Carlos, CA (US); John W Gaiser, Mountain View, CA (US); Rachel Croft, San Francisco, CA (US)

(73) Assignee: Respiratory Diagnostics, Inc., Redmond, WA (US)

( * ) Notice: Subject to any disclaimer, the term of this patent is extended or adjusted under 35 U.S.C. 154(b) by 206 days.

This patent is subject to a terminal disclaimer.

(21) Appl. No.: 10/912,329

(22) Filed: Aug. 5, 2004

(65) Prior Publication Data

US 2005/0010162 A1 Jan. 13, 2005

Related U.S. Application Data

(60) Division of application No. 09/994,379, filed on Nov. 26, 2001, now Pat. No. 6,802,841, which is a continuation-in-part of application No. 09/304,737, filed on May 4, 1999, now Pat. No. 6,464,697, and a continuation-in-part of application No. 09/556,169, filed on Apr. 21, 2000, now Pat. No. 6,645,201, and a continuation-in-part of application No. 09/090,794, filed on Jun. 4, 1998, now abandoned.

(60) Provisional application No. 60/143,749, filed on Jul. 14, 1999.

(51) Int. Cl.
*A61B 19/00* (2006.01)
*A61B 18/18* (2006.01)

(52) U.S. Cl. .......................... 128/898; 606/41; 607/133

(58) Field of Classification Search ................... 606/41, 606/42, 45, 46, 48–50; 607/100–102, 116, 607/133; 128/898; 604/20–22
See application file for complete search history.

(56) References Cited

U.S. PATENT DOCUMENTS 1,798,902 A 3/1931 Raney
(Continued)

FOREIGN PATENT DOCUMENTS

DE 43 03 882 2/1995
(Continued)

OTHER PUBLICATIONS

Castell, D.O. "Gastroesophageal Reflux Disease: Current Strategies for Patient Management." Arch Fam Med. 5(4): 221-7.
(Continued)

*Primary Examiner*—Michael Peffley
(74) *Attorney, Agent, or Firm*—Ryan Kromholz & Manion S.C.

(57) ABSTRACT

Systems and methods apply a selected treatment agent or agents into contact with tissue at or in the region of a dysfunctional sphincter (in the case of GERD, fecal incontinence, or other dysfunctional sphincter disorders) to affect improved sphincter barrier function and/or to disrupt abnormal nerve pathways. The treatment agent can include at least one cytokine and/or at least one tissue bulking agent and/or at least one vanilloid compound to evoke a desired tissue response. The systems and methods can be used a primary treatment modality, or applied as a supplementary treatment before, during or after a primary intervention.

4 Claims, 10 Drawing Sheets

U.S. PATENT DOCUMENTS

| | | |
|---|---|---|
| 3,517,128 A | 6/1970 | Hines |
| 3,901,241 A | 8/1975 | Allen, Jr. |
| 4,011,872 A | 3/1977 | Komiya |
| 4,196,724 A | 4/1980 | Wirt et al. |
| 4,313,958 A | 2/1982 | LaHann |
| 4,411,266 A | 10/1983 | Cosman |
| 4,423,812 A | 1/1984 | Sato |
| 4,532,924 A | 8/1985 | Auth et al. |
| 4,565,200 A | 1/1986 | Cosman |
| 4,705,041 A | 11/1987 | Kim |
| 4,901,737 A | 2/1990 | Toone |
| 4,906,203 A | 3/1990 | Margrave et al. |
| 4,907,589 A | 3/1990 | Cosman |
| 4,939,149 A | 7/1990 | Blumberg |
| 4,943,290 A | 7/1990 | Rexroth et al. |
| 4,947,842 A | 8/1990 | Marchosky et al. |
| 4,955,377 A | 9/1990 | Lennox et al. |
| 4,966,597 A | 10/1990 | Cosman |
| 4,976,711 A | 12/1990 | Parins et al. |
| 5,019,075 A | 5/1991 | Spears et al. |
| 5,021,450 A | 6/1991 | Blumberg |
| 5,035,696 A | 7/1991 | Rydell |
| 5,046,512 A | 9/1991 | Murchie |
| 5,047,028 A | 9/1991 | Qian |
| 5,057,107 A | 10/1991 | Parins et al. |
| 5,078,717 A | 1/1992 | Parins et al. |
| 5,083,565 A | 1/1992 | Parins |
| 5,084,044 A | 1/1992 | Quint |
| 5,088,979 A | 2/1992 | Filipi et al. |
| 5,094,233 A | 3/1992 | Brennan |
| 5,100,423 A | 3/1992 | Fearnot |
| 5,106,360 A | 4/1992 | Ishiwara et al. |
| 5,122,137 A | 6/1992 | Lennox |
| 5,125,928 A | 6/1992 | Parins et al. |
| 5,156,151 A | 10/1992 | Imran |
| 5,190,541 A | 3/1993 | Abele et al. |
| 5,197,963 A | 3/1993 | Parins |
| 5,197,964 A | 3/1993 | Parins |
| 5,205,287 A | 4/1993 | Erbel et al. |
| 5,215,103 A | 6/1993 | Desai |
| 5,232,444 A | 8/1993 | Just et al. |
| 5,236,413 A | 8/1993 | Fiering |
| 5,242,441 A | 9/1993 | Avitall |
| 5,254,126 A | 10/1993 | Filipi et al. |
| 5,256,138 A | 10/1993 | Vurek et al. |
| 5,257,451 A | 11/1993 | Edwards et al. |
| 5,263,493 A | 11/1993 | Avitall |
| 5,275,162 A | 1/1994 | Edwards et al. |
| 5,275,608 A | 1/1994 | Forman et al. |
| 5,275,610 A | 1/1994 | Eberbach |
| 5,277,201 A | 1/1994 | Stern |
| 5,281,216 A | 1/1994 | Klicek |
| 5,281,217 A | 1/1994 | Edwards et al. |
| 5,281,218 A | 1/1994 | Imran |
| 5,290,286 A | 3/1994 | Parins |
| 5,292,321 A | 3/1994 | Lee |
| 5,293,869 A | 3/1994 | Edwards et al. |
| 5,309,910 A | 5/1994 | Edwards et al. |
| 5,313,943 A | 5/1994 | Houser et al. |
| 5,314,466 A | 5/1994 | Stern et al. |
| 5,316,020 A | 5/1994 | Truffer |
| 5,324,284 A | 6/1994 | Imran |
| 5,328,467 A | 7/1994 | Edwards et al. |
| 5,334,196 A | 8/1994 | Scott et al. |
| 5,336,222 A | 8/1994 | Durgin, Jr. et al. |
| 5,345,936 A | 9/1994 | Pomeranz et al. |
| 5,348,554 A | 9/1994 | Imran et al. |
| 5,363,861 A | 11/1994 | Edwards et al. |
| 5,365,926 A | 11/1994 | Desai |
| 5,365,945 A | 11/1994 | Halstrom |
| 5,366,490 A | 11/1994 | Edwards et al. |
| 5,368,557 A | 11/1994 | Nita et al. |
| 5,368,592 A | 11/1994 | Stern et al. |
| 5,370,675 A | 12/1994 | Edwards et al. |
| 5,370,678 A | 12/1994 | Edwards et al. |
| 5,383,876 A | 1/1995 | Nardella |
| 5,383,917 A | 1/1995 | Desai et al. |
| 5,385,544 A | 1/1995 | Edwards et al. |
| 5,397,339 A | 3/1995 | Desai |
| 5,398,683 A | 3/1995 | Edwards et al. |
| 5,401,272 A | 3/1995 | Perkins |
| 5,403,311 A | 4/1995 | Abele et al. |
| 5,409,453 A | 4/1995 | Lundquist et al. |
| 5,409,483 A | 4/1995 | Campbell et al. |
| 5,415,657 A | 5/1995 | Taymor-Luia |
| 5,421,819 A | 6/1995 | Edwards et al. |
| 5,423,808 A | 6/1995 | Edwards et al. |
| 5,423,812 A | 6/1995 | Ellman et al. |
| 5,431,914 A | 7/1995 | Adekunle et al. |
| 5,433,739 A | 7/1995 | Sluijter et al. |
| 5,435,805 A | 7/1995 | Edwards |
| 5,441,499 A | 8/1995 | Fritzsch |
| 5,443,470 A | 8/1995 | Stern et al. |
| 5,454,782 A | 10/1995 | Perkins |
| 5,456,662 A | 10/1995 | Edwards et al. |
| 5,456,682 A | 10/1995 | Edwards et al. |
| 5,458,596 A | 10/1995 | Lax et al. |
| 5,458,597 A | 10/1995 | Edwards et al. |
| 5,465,717 A | 11/1995 | Imran et al. |
| 5,470,308 A | 11/1995 | Edwards et al. |
| 5,471,982 A | 12/1995 | Edwards et al. |
| 5,472,441 A | 12/1995 | Edwards et al. |
| 5,484,400 A | 1/1996 | Edwards et al. |
| 5,486,161 A | 1/1996 | Lax et al. |
| 5,490,984 A | 2/1996 | Freed |
| 5,496,271 A | 3/1996 | Burton et al. |
| 5,496,311 A | 3/1996 | Abele et al. |
| 5,500,012 A | 3/1996 | Brucker et al. |
| 5,505,728 A | 4/1996 | Ellman et al. |
| 5,505,730 A | 4/1996 | Edwards |
| 5,507,743 A | 4/1996 | Edwards et al. |
| 5,509,419 A | 4/1996 | Edwards et al. |
| 5,514,130 A | 5/1996 | Baker |
| 5,514,131 A | 5/1996 | Edwards et al. |
| 5,520,684 A | 5/1996 | Imran |
| 5,531,676 A | 7/1996 | Edwards et al. |
| 5,531,677 A | 7/1996 | Lundquist et al. |
| 5,536,240 A | 7/1996 | Edwards et al. |
| 5,536,267 A | 7/1996 | Edwards et al. |
| 5,540,655 A | 7/1996 | Edwards et al. |
| 5,549,644 A | 8/1996 | Lundquist et al. |
| 5,554,110 A | 9/1996 | Edwards et al. |
| 5,556,377 A | 9/1996 | Rosen et al. |
| 5,558,672 A | 9/1996 | Edwards et al. |
| 5,558,673 A | 9/1996 | Edwards et al. |
| 5,562,720 A | 10/1996 | Stern et al. |
| 5,571,116 A | 11/1996 | Bolanos et al. |
| 5,578,007 A | 11/1996 | Imran |
| 5,588,432 A | 12/1996 | Crowley |
| 5,588,960 A | 12/1996 | Edwards et al. |
| 5,599,345 A | 2/1997 | Edwards et al. |
| 5,599,346 A | 2/1997 | Edwards et al. |
| 5,609,151 A | 3/1997 | Mulier et al. |
| 5,624,439 A | 4/1997 | Edwards et al. |
| 5,672,153 A | 9/1997 | Lax et al. |
| 5,676,674 A | 10/1997 | Bolanos et al. |
| 5,686,425 A | 11/1997 | Lee |
| 5,688,266 A | 11/1997 | Edwards et al. |
| 5,688,490 A | 11/1997 | Tournier et al. |
| 5,702,438 A | 12/1997 | Avitall |
| 5,709,224 A | 1/1998 | Behl et al. |
| 5,713,891 A | 2/1998 | Poppas |
| 5,732,698 A | 3/1998 | Swanson et al. |
| 5,738,096 A | 4/1998 | Ben-Haim |

| | | | |
|---|---|---|---|
| 5,823,197 A | 10/1998 | Edwards | |
| 5,830,213 A | 11/1998 | Panescu et al. | |
| 5,836,874 A | 11/1998 | Swanson et al. | |
| 5,840,762 A | 11/1998 | Bernstein et al. | |
| 5,860,974 A | 1/1999 | Abele | |
| 5,871,483 A | 2/1999 | Jackson et al. | |
| 5,962,532 A | 10/1999 | Campbell et al. | |
| 6,006,755 A | 12/1999 | Edwards | |
| 6,044,846 A | 4/2000 | Edwards | |
| 6,056,744 A | 5/2000 | Edwards | |
| 6,073,052 A | 6/2000 | Zelickson et al. | |
| 6,077,257 A | 6/2000 | Edwards et al. | |
| 6,156,032 A * | 12/2000 | Lennox | 606/41 |
| 6,180,658 B1 | 1/2001 | Anzalone | |
| 6,201,014 B1 * | 3/2001 | Gardiner | 514/463 |
| 6,238,335 B1 | 5/2001 | Silverman et al. | |
| 6,238,872 B1 | 5/2001 | Mosseri | |
| 6,251,063 B1 | 6/2001 | Silverman et al. | |
| 6,251,064 B1 | 6/2001 | Silverman et al. | |
| 6,358,197 B1 | 3/2002 | Silverman et al. | |
| 6,358,245 B1 | 3/2002 | Edwards et al. | |
| 6,440,128 B1 | 8/2002 | Edwards et al. | |
| 6,464,697 B1 | 10/2002 | Edwards et al. | |
| 2001/0006982 A1 | 7/2001 | Cruz et al. | |
| 2004/0039052 A1 | 2/2004 | Cruz et al. | |

FOREIGN PATENT DOCUMENTS

| | | |
|---|---|---|
| DE | 38 38 840 | 2/1997 |
| EP | 0 139 607 | 5/1985 |
| EP | 0 401 903 | 5/1990 |
| EP | 0 608 609 | 8/1994 |
| WO | 91/01773 | 2/1991 |
| WO | 92/10142 | 6/1992 |
| WO | 93/08755 | 5/1993 |
| WO | 94/10925 | 5/1994 |
| WO | 94/21165 | 9/1994 |
| WO | 94/21178 | 9/1994 |
| WO | 94/22366 | 10/1994 |
| WO | 94/26178 | 11/1994 |
| WO | 95/18575 | 7/1995 |
| WO | 95/19142 | 7/1995 |
| WO | 95/25472 | 9/1995 |
| WO | 96/00042 | 1/1996 |
| WO | 96/16606 | 6/1996 |
| WO | 96/29946 | 10/1996 |
| WO | 96/40079 | 12/1996 |
| WO | 97/06857 | 2/1997 |
| WO | 97/32532 | 9/1997 |
| WO | 97/43971 | 11/1997 |

OTHER PUBLICATIONS

Dallemagne, B., et al.; "Laparoscopic Nissen Fundoplication: Preliminary." Surgical Laparoscopy & Endoscopy. 1991 1(3): 138-43.

Hinder, R.A., et al.; "The Technique of Laparoscopic Nissen Fundoplication: Surgical Laparoscopy and Endoscopy." 1992.2(3): 265-272.

Karlstrom, L.H. et al.; "Ectopic Jejunal Pacemakers and Enterogastric Reflux Roux Gastrectomy: Effect of Intestinal Pacing." Surgery 1989. 106(3): 486-495.

Kelly, K..A. et al.; "Duodenal-Gastric Reflux and Slowed Gastric Emptying by Electrical Pacing of the Canine Duodenal Pacesetter Po-tential." Gastroenterology. 1977. 72(3): 429-33.

Urshel, J.D.; "Complications of Antireflux Surgery." Am. J Surg. 1993. 166(1): 68-70.

Kaneko, et al.; "Physiological Laryngeal Pacemaker" May 1985. Trans Am Soc. Artif Intern Organs, vol. XXXI, pp. 293-296.

Mugica et al.; Neurostimulation: An Overview, Chapter 21, Preliminary Test of a Muscular Diaphragm Pacing System on Human Patients. 1985. pp. 3. 263-279.

Rice et al.; Endoscopic Paranasal Sinus Surgery, Chapter 5, Functional Endoscopic Paranasal Sinus Surgery, The Technique of Messerklinger; Raven Press, 1988, pp. 75-104.

Rice et al.; Endoscopic Parsanasal Sinus Surgery, Chapter 6, Total Endoscopic Sphenoethmoidectomy, The Technique of Wigand; Raven Press, 1988, pp. 105-125.

Reynolds, J.C.; "Influence of Pathophysiology, Severity, and Cost on the Medical Management of Gastroesophageal Reflux Disease." Am J Health-Syst Phar. 53(22Supl3): S5-12.

Mugica et al; "Direct Diaphragm Stimulation," Jan. 1987 PACE, vol. 10, pp. 252-256.

* cited by examiner

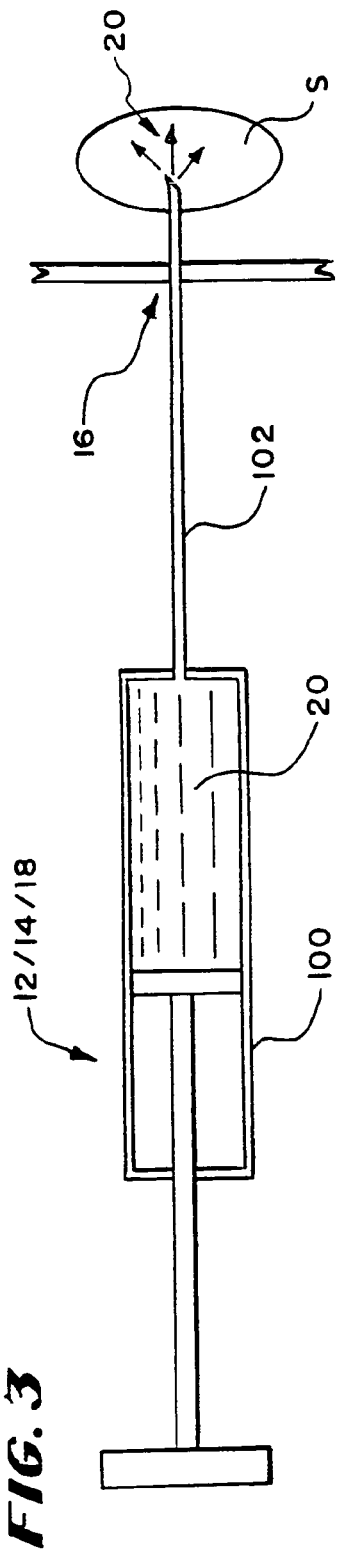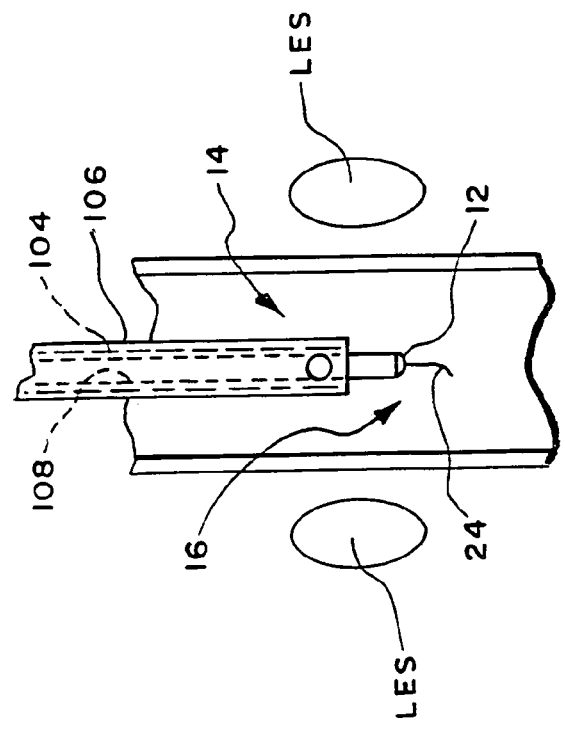
FIG. 3
FIG. 4

SYSTEMS METHODS FOR APPLYING A SELECTED TREATMENT AGENT INTO CONTACT WITH TISSUE TO TREAT SPHINCTER DYSFUNCTION

RELATED APPLICATIONS

This application is a divisional of U.S. patent application Ser. No. 09/994,379, filed Nov. 26, 2001, now U.S. Pat. No. 6,802,841, which is a continuation-in-part of U.S. patent application Ser. No. 09/304,737, now U.S. Pat. No. 6,464,697, filed May 4, 1999, and a continuation-in-part of U.S. patent application Ser. No. 09/556,169, now U.S. Pat. No. 6,645,201, filed Apr. 21, 2000, which claims the benefit of U.S. Provisional Patent Application Ser. No. 60/143,749, filed Jul. 14, 1999, and a continuation-in-part of U.S. patent application Ser. No. 09/090,794, filed Jun. 4, 1998 and entitled "Method for Treating a Sphincter" (now abandoned).

FIELD OF THE INVENTION

In a general sense, the invention is directed to systems and methods for treating interior tissue regions of the body. More specifically, the invention is directed to systems and methods for treating dysfunction in body sphincters and adjoining tissue, e.g., in and around the lower esophageal sphincter and cardia of the stomach, or in and around the anal sphincter complex.

BACKGROUND OF THE INVENTION

Dysfunction of a sphincter in the body can lead to internal damage or disease, discomfort, or otherwise adversely affect patient quality of life.

Gastroesophageal reflux disease (GIRD), for example, is a common disorder caused most commonly by frequent transient relaxations of the lower esophageal sphincter (LES). If the lower esophageal sphincter fails to function properly, stomach contents, including acid, enzymes, and bile may flow backwards into the esophagus, causing heartburn or other disease symptoms, damage to the esophagus, and the development of precancerous lesions.

Fecal incontinence is the involuntary passage of solid or liquid stool through the anal canal. This is caused most commonly by previous damage to or aging of the external and/or internal sphincter muscles in the anal canal. Secondary causes are improper sensing and control of solid or liquid stool within the rectum.

The disease states of GERD and fecal incontinence have in common a defective sphincter barrier as a mechanism of the disease. The end result is the development of GERD and fecal incontinence symptoms due to inadequate barrier function. In both GERD and fecal incontinence, inadequate barrier function can be the result of either a mechanical defect in the sphincter, a low resting pressure in the sphincter, an overly compliant sphincter, abnormal afferent nerve impulses that trigger transient sphincter relaxations, or improper sensing of and control of lumenal contents.

SUMMARY OF THE INVENTION

The invention provides systems and methods that apply a selected treatment agent into contact with tissue at, or in, the region of a dysfunctional sphincter in order to affect improved sphincter barrier function and improve a disease state. The systems and methods may be used as either a primary treatment modality, or applied as a supplementary treatment before, during or after a primary intervention.

According to one aspect of the invention, the treatment agent includes at least one sub-type of a cytokine. Delivery of a cytokine to tissue evokes a desired tissue response, which can include, e.g., an initiation of a localized healing process including influx of white blood cells and fibroblasts, followed by deposition of collagen, and a subsequent reduction in tissue compliance and tightening. These effects will result in improved sphincter barrier function. The cytokine treatment agent may be applied to the surface of a tissue, or, alternatively, it may be injected below the surface of the tissue, including the submucosa, the sphincter itself, or the area surrounding the sphincter.

According to another aspect of the invention, the treatment agent may include a tissue bulking agent, which is injected into subsurface tissue, including the submucosa, the sphincter, or the area surrounding the sphincter. Presence of the bulking agent results in additional tissue compliance reduction and tightening to improve sphincter barrier function.

According to another aspect of the invention, the treatment agent includes at least one vanilloid compound. Presence of the vanilloid compound evokes a desired tissue response, which includes at least one of the following, e.g., the interruption of afferent nerve impulses which lead to impaired sphincter function or diminished pain impulses from the treated area. The vanilloid treatment agent may be applied to surface tissue, or, alternatively, it may be injected into subsurface tissue, including the submucosa, the sphincter, or the area surrounding the sphincter. In one embodiment, the systems and methods apply energy to the tissue region to form at least one lesion in conjunction with application of the treatment agent.

Features and advantages of the inventions are set forth in the following Description and Drawings, as well as in the appended claims.

BRIEF DESCRIPTION OF THE DRAWINGS

FIG. 3 is an embodiment of a tissue treatment device that takes the form of a syringe and a needle for injecting a treatment agent into a sphincter tissue region that can be visualized from outside the body, e.g., the anal sphincter complex;

FIG. 4 is an embodiment of a tissue treatment device for injecting a treatment agent into a sphincter tissue region that cannot be visualized from outside the body, e.g., in and around the LES;

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

This specification discloses various catheter-based systems and methods for treating dysfunction of sphincters and adjoining tissue regions in the body. The systems and methods are particularly well suited for treating these dysfunctions in the lower gastrointestinal tract, e.g., in the intestines, rectum and anal canal. The systems and methods are also particularly well suited for treating these dysfunctions in the upper gastrointestinal tract, e.g., in the lower esophageal sphincter and adjacent cardia. For this reason, the systems and methods will be described in these contexts.

Still, it should be appreciated that the disclosed systems and methods are applicable for use in treating other dysfunctions elsewhere in the body, e.g., for restoring compliance to or otherwise tightening interior tissue or muscle regions. The systems and methods that embody features of the invention are also adaptable for use with systems and surgical techniques that are not necessarily catheter-based.

I. System Overview

Figure 1A:
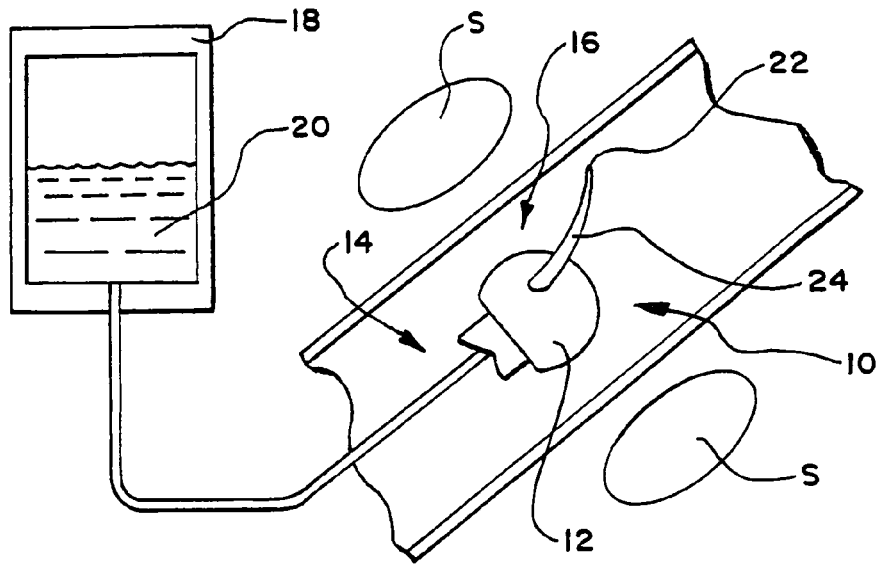
FIGS. 1A and 1B are schematic views of a system for treating tissue that includes a treatment device with a tissue piercing member that embodies features of the invention, FIG. 1A showing the treatment device deployed in a sphincter tissue region and FIG. 1B showing the treatment device piercing the tissue region to inject a treatment agent into the sphincter.
Figure 1B:
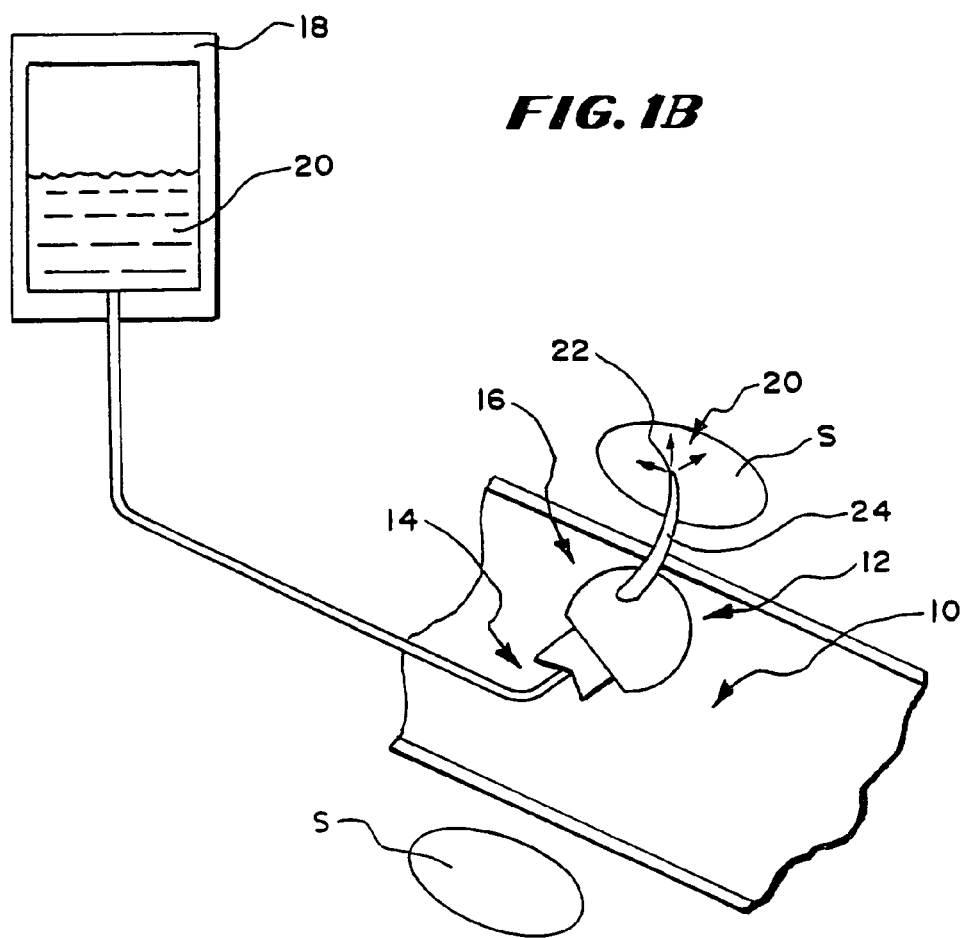

A tissue treatment system 10 that embodies features of the invention is shown in FIG. 1. The tissue treatment system 10 includes a tissue treatment device 12 and an apparatus 14 to deliver the tissue treatment device 12 to a tissue region 16 where a sphincter targeted for treatment is located. The treatment system 10 also includes a source 18 of a treatment agent 20.

A. The Tissue Treatment Device

The tissue treatment device 12 serves to apply the treatment agent 20 to the targeted sphincter tissue region 16 to obtain a desired therapeutic effect. The therapeutic effect can comprise either a physical alteration of the sphincter or tissue adjacent to the sphincter, or a neurologic alteration of nerve impulse pathways innervating the sphincter or tissue adjacent to the sphincter, or both.

The tissue treatment device 12 includes one or more agent delivery ports 22. The one or more delivery ports 22 can apply the treatment agent 20 to surface tissue in the region 16. Desirably (as FIG. 1 shows), the port 20 is located at the end of a tissue piercing member 24. In this arrangement, the treatment agent 20 may be injected into subsurface tissue, including the submucosa, the sphincter, or the area surrounding the sphincter.

Figure 2A:
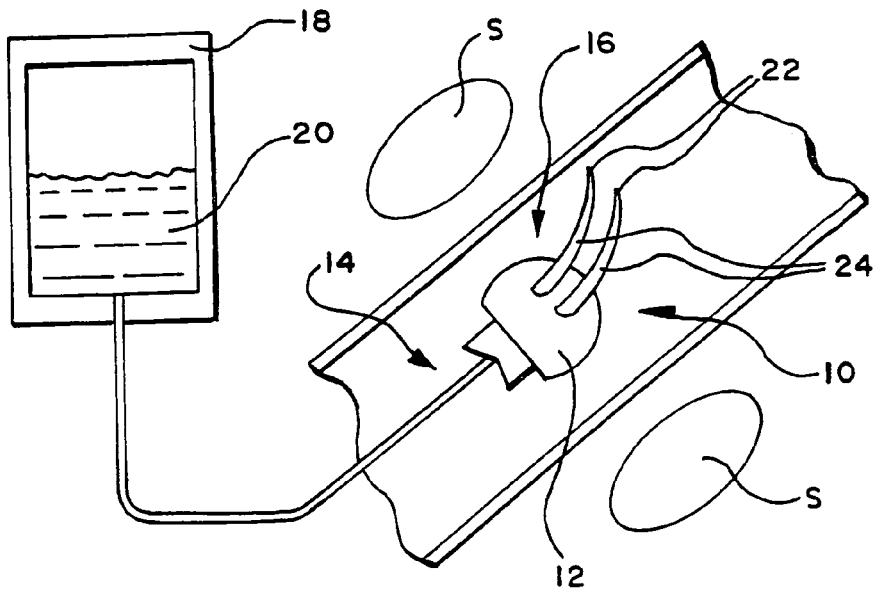
FIGS. 2A and 2B are schematic views of a system for treating tissue that includes a treatment device with multiple tissue piercing members that embodies features of the invention, FIG. 2A showing the treatment device deployed in a sphincter tissue region and FIG. 2B showing the treatment device piercing the tissue region to inject a treatment agent into the sphincter.
Figure 2B:
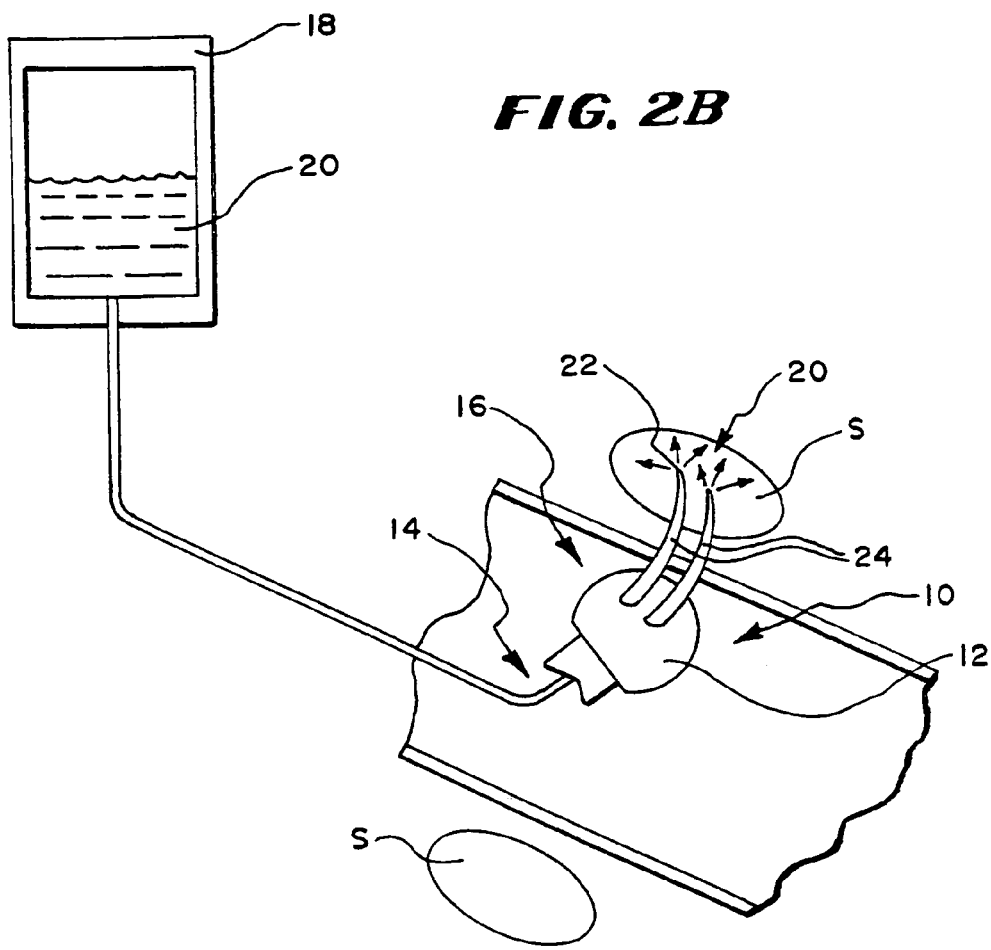

The tissue treatment device 12 can include single or multiple ports 22 located single or multiple tissue piercing members 24 to inject the treatment agent 20. As FIG. 1 shows, a single tissue piercing member 24 (with a single port 22) may be used. Alternatively, as FIG. 2 shows, the treatment device 24 can carry multiple tissue piercing members 24, each with a port 22. Desirably, the multiple tissue piercing members 24 are arranged in a spaced-apart array, to apply the treatment agent 20 in a prescribed pattern at the targeted site.

Alternatively, the tissue treatment device 12 may employ air powered, needle-less injection technology.

B. The Delivery Device

The configuration of the delivery apparatus 14 for the device 12 can also vary, depending upon the accessibility of the treatment site and the particular treatment objectives desired.

If the treatment site can be directly visualized—for example, sphincters in the anal canal—the delivery apparatus 14, the source 18, and the treatment device 12 can comprise a syringe 100 and a needle 102, as FIG. 3 shows.

If the treatment site can not be directly visualized or is otherwise not as readily accessible—for example, the LES or cardia—the delivery apparatus 14 can comprise an endoscope 106 having an interior lumen 104 passed down the esophagus through the mouth, as FIG. 4 shows. In this arrangement, the treatment device 12 is desirably carried on the distal end of a catheter tube 108 for passage through the endoscope lumen 104 to the targeted site. A guidewire may be used, if desired, to further facilitate deployment of the endoscope and treatment device to the targeted site.

As FIGS. 5 to 11 and 12 to 13 further show (and as will be described in greater detail later), the treatment device 12 can be integrated with other sphincter treatment devices, particularly if another treatment modality or therapeutic result is contemplated in combination with the application of the treatment agent 20, e.g., the formation of lesions.

C. The Tissue Treatment Agent

The treatment agent 20 is selected from a group of candidate agents based upon the physiologic effect or effects that are desired. One or more candidate agents may be applied simultaneously, or an agent(s) may be applied as a supplementary treatment before, during or after a primary intervention.

In the illustrated embodiment, the group consists essentially of three candidate agents: (1) Cytokine Sub-Types; (2) Tissue Bulking Agents; and (3) Vanilloid Compounds 1. Cytokine Subtypes The treatment agent 20 can include one or more subtypes of cytokines. A cytokine, in the natural state within the body, is a protein produced and released by a biological cell that has an effect on the local environment surrounding the cell.

Cytokines are involved in many cellular processes, such as wound healing. Application of cytokines to a sphincter could be performed with an intent to improve the barrier function. The mechanism of action would depend on the specific cytokine utilized. The term "cytokine subtype" as used herein means any polypeptide that affects the functions of other cells, and is a molecule which modulates interactions between cells in the immune or inflammatory response. A cytokine subtype includes, but is not limited to monokines and lymphokines regardless of which cells produce them. For instance, a monokine is generally referred to as being produced and secreted by a mononuclear cell, such as a macrophage and/or monocyte but many other cells produce monokines, such as natural killer cells, fibroblasts, basophils, neutrophils, endothelial cells, brain astrocytes, bone marrow stromal cells, epideral keratinocytes, and B-lymphocytes. Lymphokines are generally referred to as being produced by lymphocyte cells. Examples of cytokine subtypes include, but are not limited to, interleukin-1 (IL-1), tumor necrosis factor-alpha (TNF alpha) and tumor necrosis factor beta (TNF beta).

Other cytokine subtypes include TGF-β (transforming growth factor); PDGF (platelet derived growth factor); FGF (basic fibroblast growth factor): IGF-1 (insulin-like growth factor 1); EGF (epidermal growth factor); and VEGF. Some of these cytokines are available commercially, could be produced commercially, or can be extracted from a persons harvested platelets (platelet releasates). The effects of a given cytokine upon tissue physiology can include one or more of the following: smooth muscle and fibroblast mitogenic effects (induces division and growth of cells) stimulation of the release of cytokines from other cells; chemoattractant (bringing new healing cells into local region); decrease of collagen enzyme activity allowing collagen to build up; inflammation; and angiogenesis (development of new blood vessels).

The treatment agent 20 can include a cytokine sub-type or combination of cytokine sub-types, alone or in combination with other substances. The cytokine-containing treatment agent can be applied by the port or ports 22 to the mucosal lining, or injected into the sphincter muscle, or applied extrinsically to the outside of the sphincter.

The cytokine-containing treatment agent 20 can be a solution, a gel, a powder, a pellet, or other form. The treatment agent may be released immediately, or, be a sustained release product such as a slow released implant, slow release gel, coated pellet, microsphere, or other form.

The cytokine-containing agent 20 may be applied or injected as primary therapy, or applied as a supplementary treatment before, during or after a primary intervention. For example, as will be described later, radio frequency (RF) energy may be used to induce the wound healing process, followed by cytokine application to facilitate more exuberant wound healing.

The application of a single cytokine or mixture thereof, as primary, neoadjuvant, or adjuvant therapy for a sphincter disease could have the various mechanical and therapeutic effects. With or without an inciting wound event (such as RF), cytokines can serve to initiate the process of healing within the local region. This process includes, but is not limited to, influx of white blood cells and macrophages, stimulation of fibroblast and smooth muscle division and collagen secretion, new blood vessel growth, wound contraction and tightening, maturation of the new or existing collagen framework, and reduced tissue compliance. These tissue effects could improve the barrier function of defective sphincter complexes in GERD, fecal incontinence, and other possible disorders.

Examples of cytokine materials that can be used include commercially available Regranex, which is recombinant human PDGF-BB. This material has been applied as a gel for promoting the healing of diabetic foot ulcers. Platelet granules contain many of the cytokines listed above, and the cytokines can be extracted with a fairly simple technique (platelet releasates technique). Platelets (harvested as a pooled platelet product or from autologous donation) provide a source of cytokines for extraction. TGF-β and PDGF are considered to be the most important substances for the purpose of initiating the wound healing process.

2. Tissue Bulking Agents

The treatment agent 20 can include one or more tissue bulking agents. Examples of tissue bulking agents that can be used include collagen, dermis, cadaver allograft material, or ePTFE (expanded poly-tetrafluoroethyene) pellets.

The tissue bulking treatment agent 20 can be injected by the port or ports 22 into the sphincter muscle, or applied extrinsically to the outside of the sphincter.

The tissue bulking treatment agent 20 may be applied or injected as primary therapy, or applied as a supplementary treatment before, during or after a primary intervention. For example, as will be described later, radio frequency (RF) energy can be applied to the injected bulking agent 20 to change its physical characteristics, e.g., to expand or harden the bulking material, to achieve a desired effect.

3. Vanilloids and Related Substances

The treatment agent 20 can comprise a vanilloid compound. Vanilloid compounds have a unique capacity to bind to a membrane receptor in sensory neurons. Capsaicin is one of many vanilloid compounds. Capsaicin is a powerful basic compound which is derived from chili peppers.

The specific neuron for capsaicin is deemed "VR1". This receptor is expressed only on small unmyelinated C-fibers (nerves typically involved in special visceral sensation and pain)

Exposure to vanilloid compounds variably reduces the responsiveness of the neuron to stimuli. In many cases, the neuron may actually degenerate temporarily or permanently, thus impairing transmission of pain signals or other special sensory signals.

The term "vanilloid compound" as used herein means a compound or a mixture of compounds having a biologically active vanillyl group. Vanilloid compounds include both naturally occurring vanilloids, synthetic vanilloids, pharmaceutically acceptable salts of the vanilloid compound (whether natural or synthetic) as well as pharmaceutically acceptable derivatives and/or analogues thereof (whether natural or synthetic).

Examples of natural vanilloid compounds include both the crude extracts and the purified extracts of active vanilloid compounds from: capsicum, cayenne pepper, black pepper, paprika, cinnamon, clove, mace, mustard, ginger, turmeric, papaya seed and the cactus-like plant Euphorbia resinifera.

Synthetic vanilloid compounds such as synthetic capsaicin are disclosed in WO 96/40079, which is incorporated herein by reference. The vanilloid compound family includes: Capsaicin; Dihydrotapsaicin: Nordihydrocapsaicin Homocapsaicin: Homodihydrocapsaicin. Alternatively, resiniferotoxin (RTX) is derived from the euphorbia cactus and is considered a capsaicin-like compound. This substance also activates the VR1 receptor and attenuates or eliminates afferent nerve function, although it may not illicit the rapid heat sensation that other vanilloids produce.

Other examples of vanilloid compounds include capsaicin ((E)-(N)-[(4-hydroxy-3-methoxyphenyl)-methyl]-8-methyl-6-nonenamide); eugenol (2-methoxy-4-(2-pro-penyl)phenol); zingerone (4-(4-hydroxy-3-methoxyphenyl-2-butanone); curcumin (1,7-bis(4-hydroxy-3-methoxy-phenyl)-1,6-heptadiene-3,5-dione); piperine (1-[5-(1,3-benzodioxol-5-yl)-1-oxo-2,4-pentadienyl] piperidine); resin-iferatoxin(6, 7-deepoxy-6,7-didehydro-5-deoxy-21-dephenyl-21-(phenylmethyl)-20-(4-hydroxy-3-thoxybenzene-acetate)) or pharmaceutically effective salts, analogues, derivatives or equivalents thereof. The treatment agent 20 can include capsaicin, another vanilloid compound, RTX, or combination thereof, alone or in combination with other substances (which will be generically called a vanilloid-containing treatment agent 20).

The vanilloid-containing treatment agent can be applied through the port 22 or ports 22 to the mucosal lining or extrinsically to the outside of the sphincter. The vanilloid-containing treatment agent can also be injected into the target organ wall, such as the gastric cardia and LES for the treatment of GERD or the anal sphincters for treatment of fecal incontinence.

The treatment agent 20 can be a solution, a gel, a powder, a pellet, or other form. The treatment agent may be released immediately, or, be a sustained release product such as a slow released implant, slow release gel, coated pellet, microsphere, or other form.

The vanilloid-containing treatment agent 20 may be applied or injected as primary therapy, or applied as a supplementary treatment before, during or after a primary intervention. For example, RF energy may be used to incite a wound, followed by application of the vanilloid-containing treatment agent to facilitate exuberant wound healing.

In GERD and fecal incontinence, the use of a vanilloid-containing treatment agent can serve to interrupt afferent nerve impulses could therefore be of significant therapeutic benefit. In GERD, the use of a vanilloid-containing treatment agent can serve to interrupt afferent impulses which trigger transient lower esophageal sphincter relaxations, a common mechanism for GERD.

In fecal incontinence, the use of a vanilloid-containing treatment agent can serve to potentially limit the fecal sampling reflex, which may lead to fecal leakage events. Additionally, fecal incontinence may be caused in some patients by abnormal nerve feedback pathways in the anal canal and rectum, which could be favorably modulated by application of vanilloid-containing agents.

An example of vanilloid materials that can be used is produced by Afferon and is called RTX, which has been instilled into the lumen of the urinary bladder for the treatment of urge incontinence. There are also several topical, over-the-counter capsaicin products for topical analgesic applications.

II. Devices for the Treatment of GERD

Figure 5:
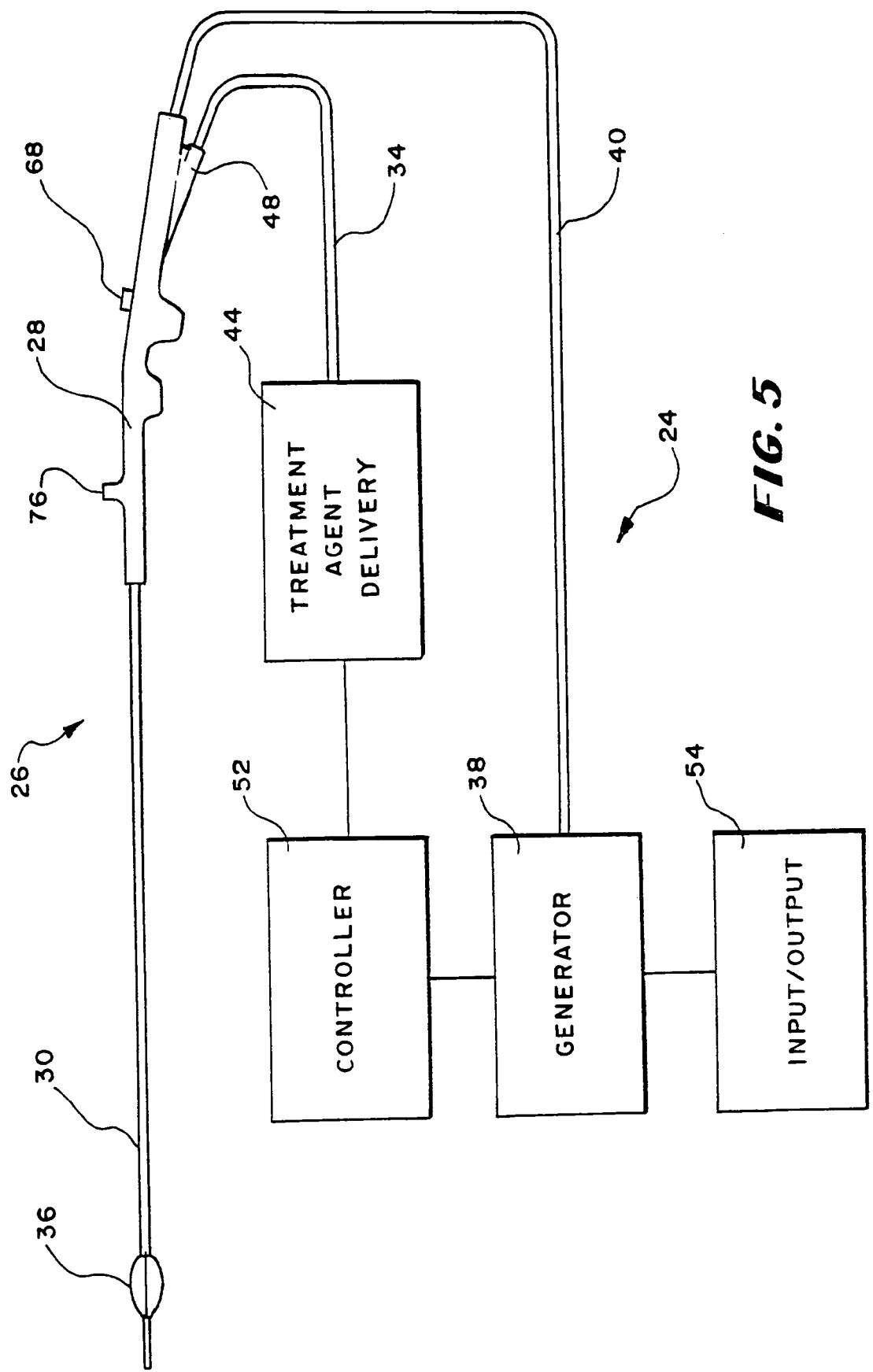
FIG. 5 is a schematic view of a system that includes an embodiment of a treatment device for injecting a treatment agent as well as forming lesions in and around the LES to treat GERD.

Another tissue treatment device 26 well suited for treating GERD by injecting one or more treatment agents 20 in tissue regions at or near the LES or cardia is shown in FIG. 5. The device 26 is also well suited for applying radio frequency energy to these tissue regions, alone or in combination with injection of the treatment agent 20, to form lesions.

The device 26 includes a handle 28 made, e.g., from molded plastic. The handle 28 carries a flexible catheter tube 30. The catheter tube 30 can be constructed, for example, using standard flexible, medical grade plastic materials, like vinyl, nylon, poly(ethylene), ionomer, poly(urethane) poly (amide), and poly(ethyleneterephthalate). The handle 28 is sized to be conveniently held by a physician, to introduce the catheter tube 30 into the tissue region targeted for treatment. The catheter tube 30 may be deployed with or without the use of a guide wire (not shown).

The catheter tube 30 carries on its distal end an operative element 36. The operative element 36 can take different forms and can be used for either therapeutic purposes, or diagnostic purposes, or both. The operative element 36 can support, for example, a device for imaging body tissue, such as an endoscope, or an ultrasound transducer. The operative element 36 can also support a device to deliver a drug or therapeutic material to body tissue. The operative element 36 can also support a device for sensing a physiological characteristic in tissue, such as electrical activity, or for transmitting energy to stimulate tissue or to form lesions in tissue.

In the illustrated embodiment (shown in greater detail in FIGS. 6, 7, and 8), one function that the operative element 36 performs is to apply one or more treatment agents 20 to a targeted sphincter or adjoining tissue. The operative element 36 can be configured to apply the treatment agent in various ways. For example, the operative element 36 can apply the treatment agent directly to mucosal tissue overlying the sphincter. Alternatively, the operative element 36 can apply the treatment agent extrinsically to the sphincter through mucosal tissue overlying the sphincter. Still alternatively, the operative element 36 can inject the treatment agent into the sphincter. In combination with any of these application modalities, the operative element 36 can apply ablation energy in a selective fashion to a targeted tissue region, to create one or more lesions, or a prescribed pattern of lesions, below the mucosal surface.

In one treatment modality, the treatment agent 20 is selected from a class of agents that lead to a physical tightening of the sphincter, for example, a cytokine subtype or a tissue bulking agent, as already described. In this arrangement, the formation of lesions by the selective application of energy can incite a wound event, which interacts with the process of healing that the treatment agent initiated, to achieve the desired physiologic result. In another treatment modality, the treatment agent is selected from a class of agents that interrupt afferent nerve impulses that trigger transient sphincter relation, or that cause pain, or that otherwise contribute to the dysfunction, for example, a vanilloid compound, as already described. In this arrangement, the formation of lesions by the selective application of energy can result in the interruption of aberrant electrical pathways that may cause spontaneous sphincter relaxation. Further details of this treatment modality will be described later.

The treatment modalities can restore normal barrier function to the sphincter.

As FIG. 5 shows, the treatment device 26 can operate as part of a system 24. The system 24 includes an external treatment agent delivery apparatus 44. A luer fitting 48 on the handle 28 couples to tubing 34 to connect the treatment device 26 to the treatment agent delivery apparatus 44, to delivery the treatment agent for discharge by or near the operative element 36. The system 24 can also include a generator 38 to supply energy to the operative element 36, if formation of lesions to augment the treatment agent is desired. A cable 40 coupled to the handle 28 conveys the generated energy to the operative element 36.

In the illustrated embodiment, the generator 38 supplies radiofrequency energy, e.g., having a frequency in the range of about 400 kHz to about 10 mHz. Of course, other forms of tissue ablation energy can be applied, e.g., coherent or incoherent light; heated or cooled fluid; resistive heating; microwave; ultrasound; a tissue ablation fluid; or cryogenic fluid.

The system 24 also desirably includes a controller 52. The controller 52 is linked to the generator 38 and the treatment agent delivery apparatus 44. The controller 52, which preferably includes an onboard central processing unit, governs the power levels, cycles, and duration that the radio frequency energy is distributed to the operative element 36, to achieve and maintain power levels appropriate to achieve the desired treatment objectives. In tandem, the controller 52 also desirably governs the delivery of the treatment agent.

The controller 52 desirably includes an input/output (I/O) device 54. The I/O device 54 allows the physician to input control and processing variables, to enable the controller to generate appropriate command signals.

A. The Operative Element

Figure 6:
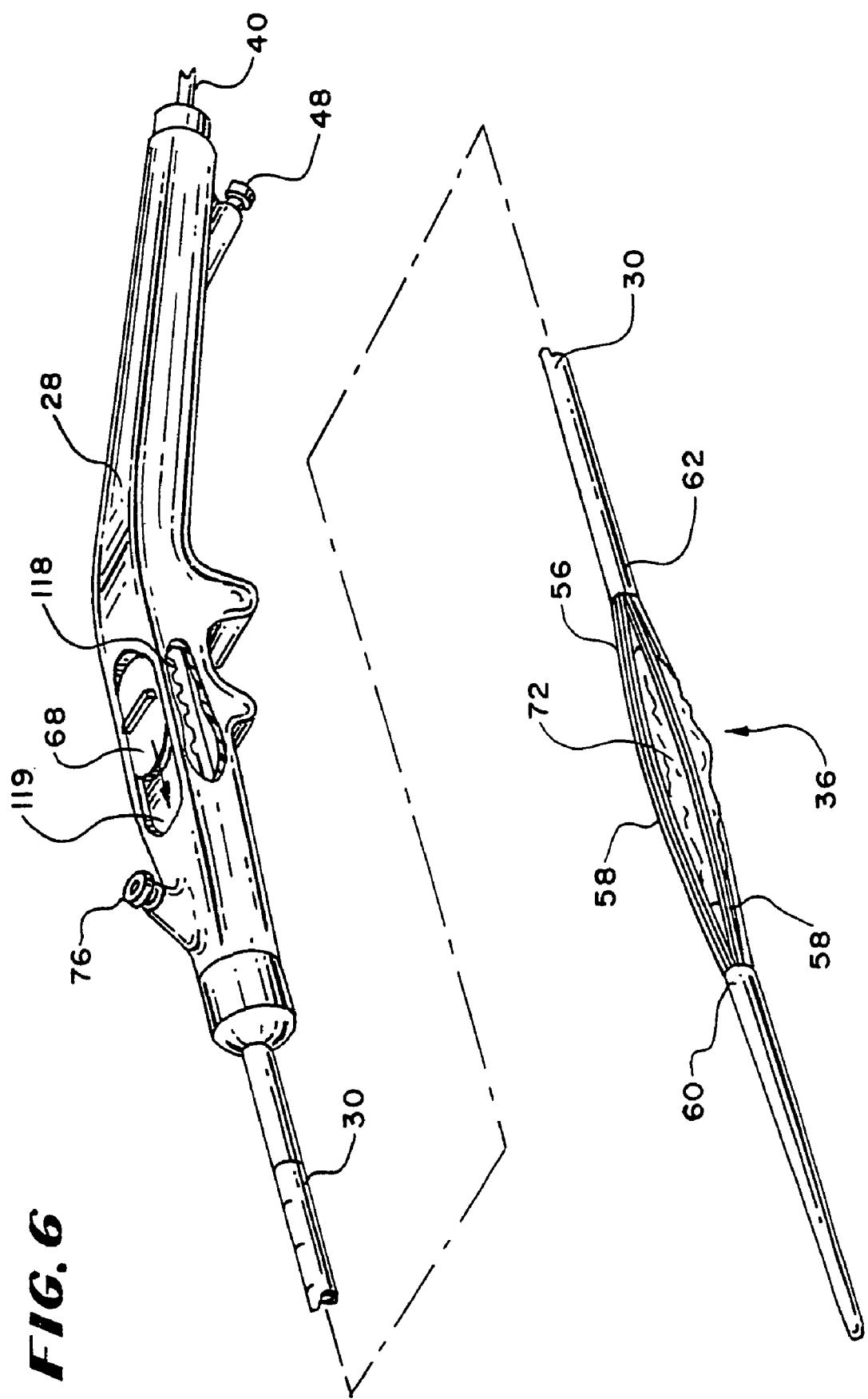
FIG. 6 is a perspective view, with portions broken away and in section, of the treatment device shown in FIG. 5, with the basket element carried by the device shown in a collapsed condition for deployment to a targeted tissue region.
Figure 7:
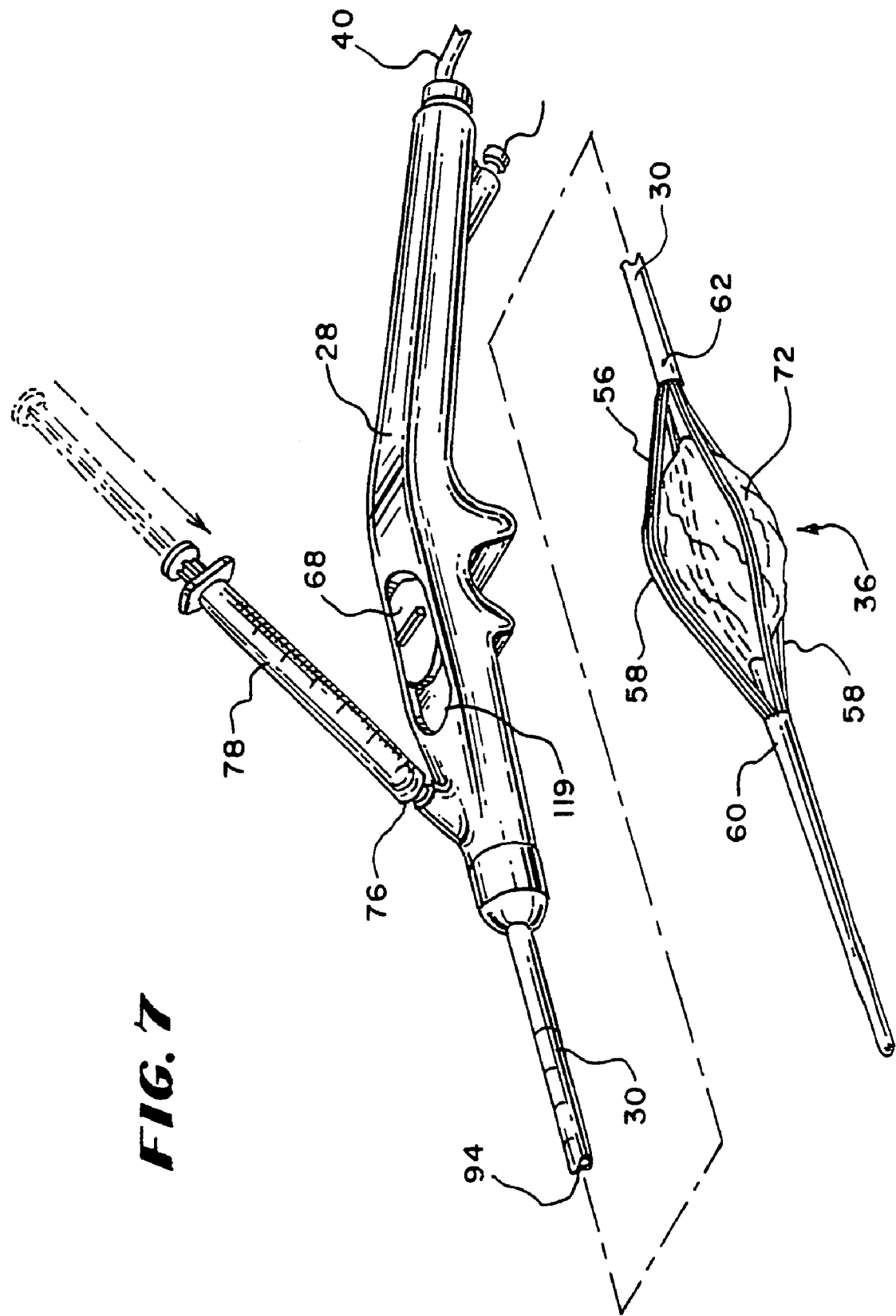
FIG. 7 is a perspective view, with portions broken away, of the treatment device shown in FIG. 5, with the basket element carried by the device shown in an expanded condition, as it would be when ready for use in a targeted tissue region.
Figure 8:
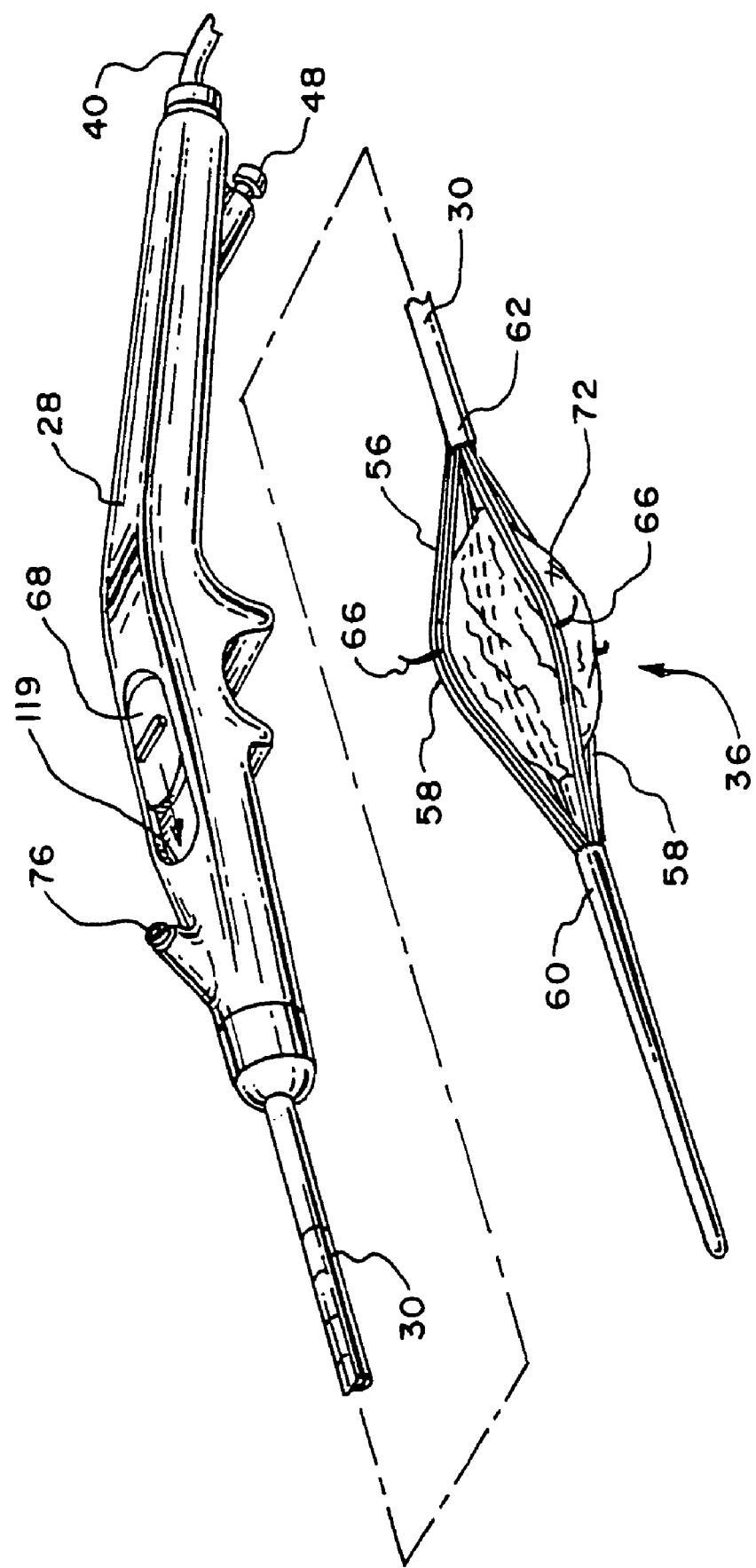
FIG. 8 is a perspective view, with portions broken away, of the treatment device shown in FIG. 5, with the basket element carried by the device shown in an expanded condition, and with electrodes carried by the basket element extended for use in a targeted tissue region.

In the embodiment shown in FIGS. 6 to 8, the operative element 36 comprises a three-dimensional basket 56. The basket 56 includes one or more spines 58, and typically includes from four to eight spines 58, which are assembled together by a distal hub 60 and a proximal base 62. In FIGS. 6 to 8, four spines 58 are shown, which are equally circumferentially spaced apart.

Each spine 58 preferably comprises a flexible body made, e.g. from molded plastic, stainless steel, or nickel titanium alloy. The cross sectional shape of the spine body 58 can vary, possessing, e.g., a circular, elliptical, square, or rectilinear shape. In the illustrated embodiment, the spine bodies 58 each possess a rectilinear shape to resist twisting.

Figure 9:
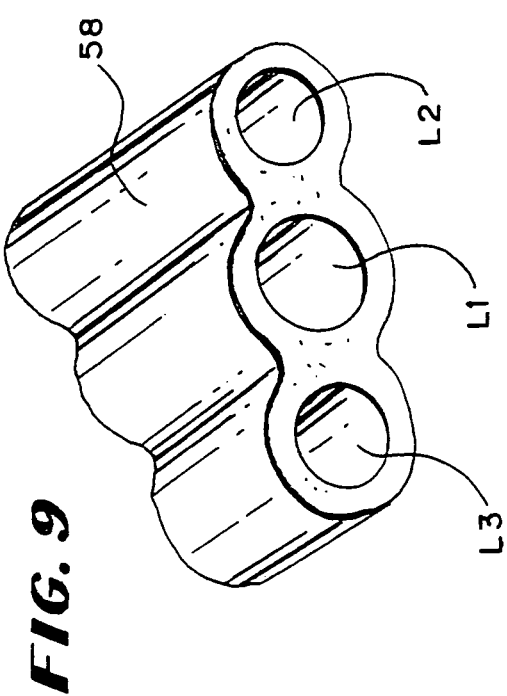
FIG. 9 is an enlarged end view of one of the multiple lumen spines that form the basket element shown in FIGS. 6 to 8, showing the multiple interior lumens that the spine possesses.
Figure 10:
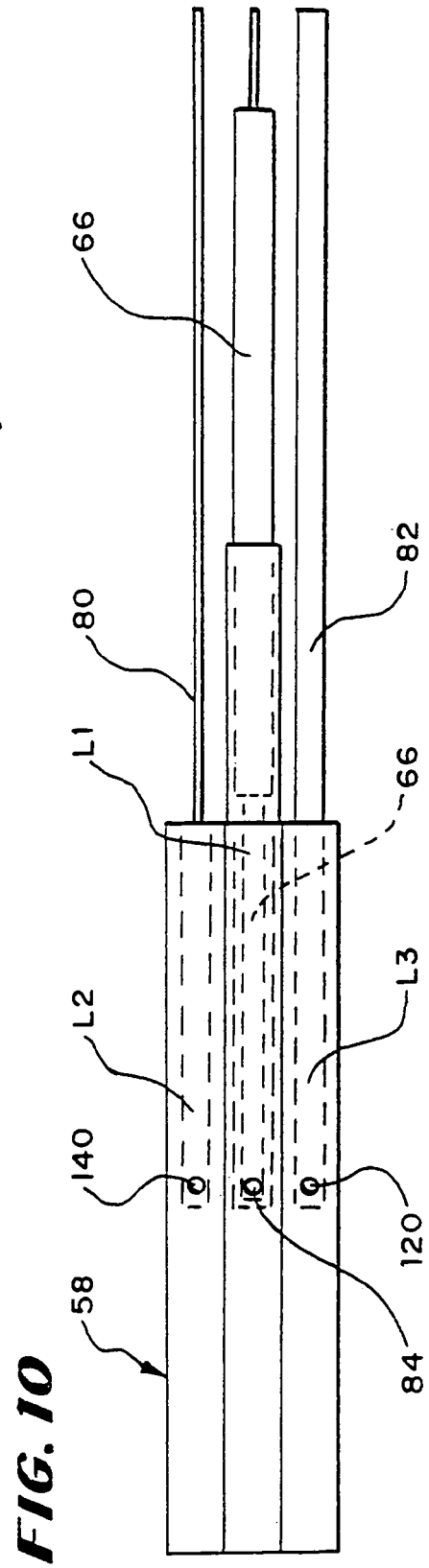
FIG. 10 is a top view of the multiple lumen spine shown in FIG. 9, showing the different functional elements that the interior lumens of the spine carry.

In the illustrated embodiment (see FIG. 9), each spine body 58 defines two or more interior lumens or passages. As FIG. 9 shows, in the illustrated embodiment, three lumens or passages, designated L1, L2, and L3, are present. For each spine 58, each passage L1, L2, and L3 is dedicated to perform a different function.

In the illustrated embodiment (see FIG. 10), a first or center passage L1 carries a movable, elongated electrode element 66. A second passage L2 along one side the first passage L1 carries a temperature sensing element 80. A third passage L3 along the opposite side of first passage L1 is coupled to tubing 82 that carries the treatment agent from the treatment agent delivery device 44.

1. The Electrodes

Figure 11:
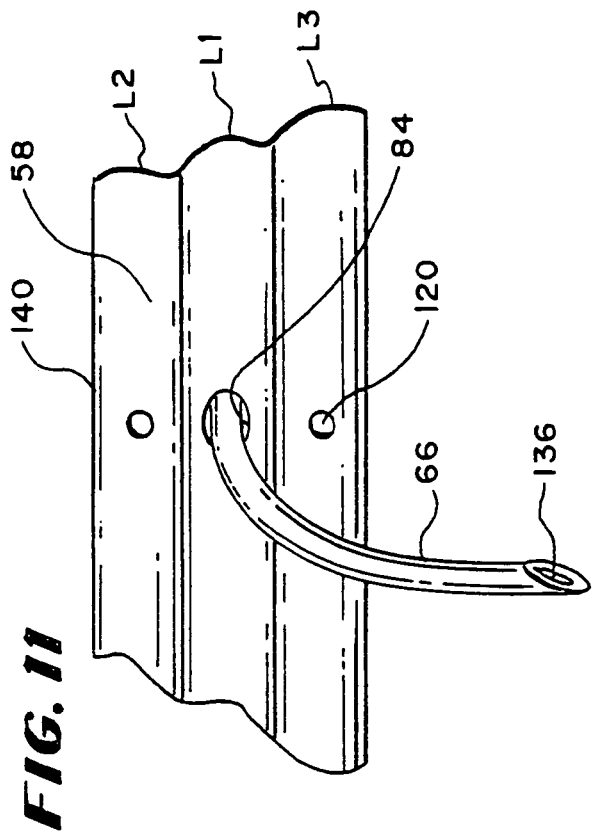
FIG. 11 is an enlarged view of a portion of one of the multiple lumen spines that form the basket element shown in FIGS. 6 to 10, showing an electrode deployed through an opening in one of the spines.

Each electrode 66 is carried within the first passage L1 for sliding movement. Each electrode 66 slides from a retracted position, withdrawn in the spine 58 (as shown in FIG. 7), and an extended position, extending outward from the spine 58 through an opening 84 in the spine 58 (as shown in FIGS. 8 and 11). A push-pull lever 68 on the handle 28 (as FIGS. 6 to 10 also show) controls the sliding movement of the electrodes with the spines 58 between the retracted position (by pulling rearward on the lever 68) and the extended position (by pushing forward on the lever 68).

As FIGS. 6 to 8 show, the lever 68 is exposed on the handle 28 for manipulation by the thumb of an operator. A suitable rachet assembly 118 (see FIG. 6) may be provided to advance the sliding movement of the lever 68 in a controlled, stepwise fashion. A slot 119 on the handle 28 stops advancement of the lever 68 beyond a predetermined distance.

In the illustrated arrangement, the electrodes 66 are intended for monopolar operation. Each electrode 66 serves as a transmitter of energy, and an indifferent patch electrode on the patient's skin (not shown) serves as a common return for all electrodes 66. It should be appreciated, however, that the operative element 36 could include bipolar pairs of electrodes 66, if desired.

In the embodiment shown in FIGS. 6 to 8, an expandable structure 72 comprising, e.g., a balloon, is located within the basket 56. The balloon structure 72 can be made, e.g., from a Polyethylene Terephthalate (PET) material, or a polyamide (non-compliant) material, or a radiation cross-linked polyethylene (semi-compliant) material, or a latex material, or a silicone material, or a C-Flex (highly compliant) material. Non-compliant materials offer the advantages of a predictable size and pressure feedback when inflated in contact with tissue. Compliant materials offer the advantages of variable sizes and shape conformance to adjacent tissue geometries.

The balloon structure 72 presents a normally, generally collapsed condition, as FIG. 6 shows. In this condition, the basket 56 is also normally collapsed about the balloon structure 72, presenting a low profile for deployment into the targeted tissue region.

The catheter tube 30 includes an interior lumen 94 (see FIG. 7), which communicates with the interior of the balloon structure 72. A fitting 76 (e.g., a syringe-activated check valve) is carried by the handle 28. The fitting 76 communicates with the lumen. The fitting 76 couples the lumen 94 to a syringe 78 (see FIG. 7), which injects fluid under pressure through the lumen 94 into the balloon structure 72, causing its expansion, as FIG. 7 shows.

Expansion of the balloon structure 72 urges the spines 58 of the basket 56 to open and expand (as FIG. 7 shows). The force exerted by the balloon structure 72 upon the spines 58, when expanded, is sufficient to exert an opening force upon the tissue surrounding the basket 56. When moved to their extended positions, the electrode 66 penetrate tissue contacted by the spines 58.

The electrodes 66 can be formed from various energy transmitting materials, e.g., nickel titanium, stainless steel (e.g., 304 stainless steel), or a combination of nickel titanium and stainless steel. The electrodes 66 have sufficient distal sharpness and strength to penetrate a desired depth into the smooth muscle of the targeted sphincter. The desired depth can range from about 4 mm to about 5 mm.

To further facilitate penetration and anchoring in the targeted tissue region, each electrode 66 is preferably biased with a bend (as FIGS. 8 and 11 show). Movement of the electrode 66 into the spine 58 overcomes the bias and straightens the electrode 66 for passage through the lumen L1. An electrical insulating material (not shown) is desirably coated about the distal end of each electrode 66, a distance below the distal tip. When the distal end of the electrode 66 that penetrates the targeted tissue region transmits radio frequency energy, the material insulates the surface of the tissue region from direct exposure to the radio frequency energy.

B. Application of the Treatment Agent

In the illustrated embodiment, the treatment agent delivery apparatus 44 conveys a selected treatment agent 20 through the third passage 13 in the spine 58 for discharge at the treatment site. The third passage 13 conveys the selected treatment agent from the apparatus 44 through an opening 120 formed in the spine 58. The opening 120 in each spine 58 is generally aligned with the needle opening 84 in the spine 58 (see FIG. 8), so that ablation and application of treatment agent 20 can occur in the same general tissue region. In this arrangement, the treatment agent can be applied either directly to mucosal tissue overlying the targeted sphincter, or extrinsically to the sphincter through mucosal tissue overlying the sphincter.

A given electrode 66 deployed by the operative device in a sphincter can also be used to inject the treatment agent 20 into the sphincter. In this arrangement, the electrode 66 includes an interior lumen 136 (see FIG. 11). In this arrangement, the treatment agent delivery apparatus 44 is coupled to the lumen 136.

C. Temperature Sensing

In the illustrated embodiment (see FIGS. 10 and 11), the second passage 12 in each spine 58 carries a temperature sensing element 80. In the illustrated embodiment, the temperature sensing element 80 comprises a thermocouple assembly. The temperature sensor is exposed through an opening 140 in the spine body 38. The temperature sensor rests against surface tissue when the basket structure is deployed for use. Desirably (as FIG. 11 shows), the temperature sensor opening 140 is generally aligned with the electrode and treatment agent openings 84 and 120, so that ablation, temperature sensing, and application of treatment agent occur generally in the same localized tissue region.

III. Devices for the Treatment of Fecal Incontinence

Figure 12:
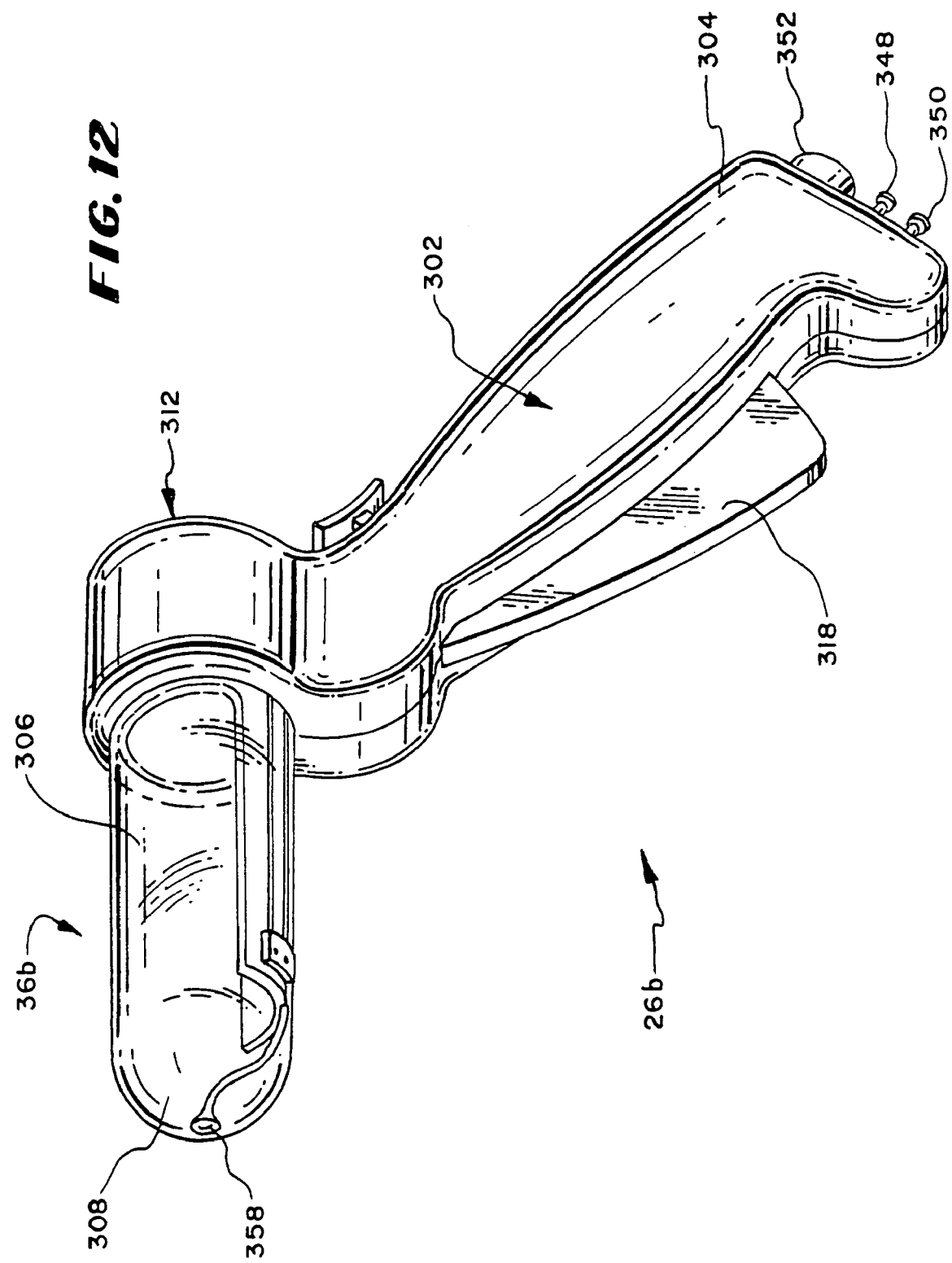
FIG. 12 is a perspective view of an embodiment of a treatment device for injecting a treatment agent as well as forming lesions in and around tissue in the lower gastrointestinal tract, the treatment device having an array of electrodes shown in a retracted position.
Figure 13:
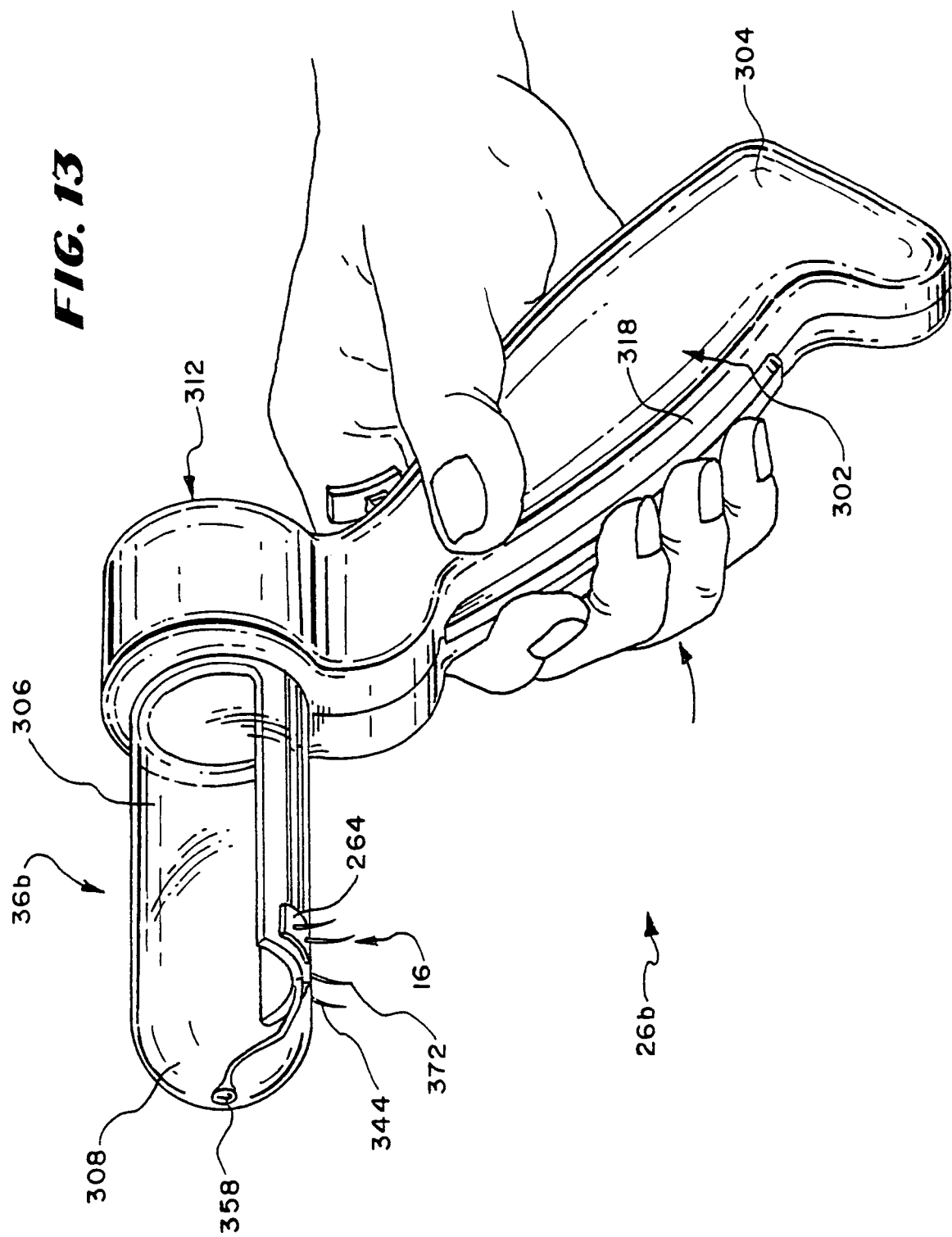
FIG. 13 is a perspective view of the device shown in FIG. 5, with the array of electrodes shown in their extended position.

FIGS. 12 and 13 show another tissue treatment device 302 well suited for injecting one or more treatment agents 20 in tissue regions at or near sphincter regions in the lower gastrointestinal tract. More particularly, the device 302 is well suited for injecting the treatment agent 20 at or near the internal and/or external sphincter muscles in the anal canal to treat fecal incontinence. The device 302 is also well suited for applying radio frequency energy to these tissue regions, alone or in combination with injection of the treatment agent 20, to form lesions.

As FIGS. 12 and 13 show, the device 302 includes a hand grip 304 that carries an operative element 36b. In the illustrated embodiment, the operative element 36b takes the form of a hollow, tubular barrel 306 made from a transparent, molded plastic material. The barrel 306 terminates with a blunt, rounded distal end 308 to aid passage of the barrel 306 through the anal canal, without need for a separate introducer. The hand grip 304 includes a viewing port 312 for looking into the transparent, hollow interior of the barrel 306, to visualize surrounding tissue.

An array of needle electrodes 316 are movably contained in a side-by-side relationship along an arcuate segment of the barrel 306. The needle electrodes 316 are mechanically linked to a finger-operated pull lever 318 on the hand grip 304. By operation of the pull lever 318, the distal ends of the needle electrodes 316 are moved between a retracted position (FIG. 12) and an extended position (FIG. 13). An electrical insulating material 344 is coated about the needle electrodes 316 (see FIG. 13), except for a prescribed region of the distal ends, where radio frequency energy is applied to tissue. The generator 38 is coupled via the cable 10 to a connector 352, to convey radio frequency energy to the electrodes 316.

In use, the physician grasps the hand grip 304 and guides the barrel 306 into the anal canal 320. The pull lever 318 is in the neutral position and not depressed, so the needle electrodes 316 occupy their normal retracted position, looking through the viewing port 312, the physician visualizes the pectinate (dentate) line through the barrel 306. Looking through the barrel 306, the physician positions the distal ends of the needle electrodes 316 at a desired location above the pectinate (dentate) line. A fiberoptic can also be inserted into the barrel 306 to provide local illumination, or the physician can wear a headlamp for this purpose. Once the distal end of the barrel 306 is located at the targeted site, the physician depresses the pull lever 318. The needle electrodes 316 advance to their extended positions. The distal ends of the electrodes 316 pierce and pass through the mucosal tissue into the muscle tissue of the target sphincter muscle. The distal end of the electrodes 316 can, e.g., penetrate the involuntary, internal sphincter muscle. The physician commands the controller 52 to apply radio frequency energy through the needle electrodes 316. The energy can be applied simultaneously by all electrodes 316, or in any desired sequence.

The treatment agent delivery apparatus 44 is coupled via tubing 12 to a connector 348 to convey the treatment agent 20, e.g., through holes in the barrel 306, to contact tissue at a localized position surrounding the electrodes 316. In this arrangement, the treatment agent 20 can be applied either directly to mucosal tissue overlying the targeted sphincter, or extrinsically to the sphincter through mucosal tissue overlying the sphincter.

Alternatively, one or more electrodes 316 deployed by the operative device in a sphincter can also be used to inject the treatment agent 20 into the sphincter. In this arrangement, the electrode 316 includes an interior lumen. In this arrangement, the treatment agent delivery apparatus 44 is coupled to the lumen 136.

The barrel 306 (see FIG. 13) also preferably carries temperature sensor 364, one of which is associated with each needle electrode 316. The sensors 364 sense tissue temperature conditions in the region adjacent to each needle electrode 316. Preferably, the distal end of each needle electrode 316 also carries a temperature sensor 372 (see FIG. 13).

Further details of the construction and use of the device 26b and other devices that can be deployed to treat sphincter regions in the lower gastro-intestinal tract are disclosed in co-pending U.S. patent application Ser. No. 09/305,123, filed Apr. 21, 2000, and entitled "Systems and Methods for Treating Dysfunctions in the Intestines and Rectum," which is incorporated herein by reference.

Various features of the invention are set forth in the following claims.

We claim:

1. A method of treating fecal incontinence comprising
   selecting at least one vanilloid compound,
   providing a source of the at least one vanilloid compound,
   selecting a targeted tissue region at or near an anal sphincter,
   deploying a catheter carrying on its distal end a tissue piercing element adjacent the targeted tissue region,
   coupling the catheter to the source of the at least one vanilloid compound,
   manipulating the tissue piercing element to enter subsurface tissue in the targeted tissue region,
   injecting through the tissue piercing element the at least one vanilloid compound into the subsurface tissue.

2. A method as in claim 1
   wherein injection of the at least one vanilloid compound limits a fecal sampling reflex.

3. A method as in claim 1
   wherein injection of the at least one vanilloid compound modulates an abnormal nerve feedback pathway in the rectum.

4. A method as in claim 1, further comprising
   applying radiofrequency energy through the tissue piercing element to incite a wound in the subsurface tissue into which the at least one vanilloid compound is injected.

* * * * *